US009868964B2

(12) United States Patent
Josse et al.

(10) Patent No.: US 9,868,964 B2
(45) Date of Patent: Jan. 16, 2018

(54) SOLID WASTE TREATMENT WITH CONVERSION TO GAS AND ANAEROBIC DIGESTION

(71) Applicant: ANAERGIA INC., Burlington (CA)

(72) Inventors: Juan Carlos Josse, Mission Viejo, CA (US); Yaniv D. Scherson, Carlsbad, CA (US)

(73) Assignee: Anaergia Inc., Burlington (CA)

( * ) Notice: Subject to any disclaimer, the term of this patent is extended or adjusted under 35 U.S.C. 154(b) by 0 days.

(21) Appl. No.: 15/015,479

(22) Filed: Feb. 4, 2016

(65) Prior Publication Data

US 2016/0230193 A1 Aug. 11, 2016

Related U.S. Application Data

(60) Provisional application No. 62/112,948, filed on Feb. 6, 2015.

(51) Int. Cl.
| | |
|---|---|
| *C02F 11/04* | (2006.01) |
| *C12P 5/02* | (2006.01) |
| *C02F 9/00* | (2006.01) |
| *B01F 3/04* | (2006.01) |
| *B01L 3/00* | (2006.01) |
| *C02F 11/12* | (2006.01) |
| *C02F 11/10* | (2006.01) |

(52) U.S. Cl.
CPC .............. *C12P 5/023* (2013.01); *B01L 3/56* (2013.01); *C02F 9/00* (2013.01); *C02F 11/04* (2013.01); *B01F 3/04* (2013.01); *C02F 11/10* (2013.01); *C02F 11/12* (2013.01); *C02F 2303/06* (2013.01); *Y02E 50/343* (2013.01)

(58) Field of Classification Search
CPC .... C12P 5/023; B01L 3/56; C02F 9/00; C02F 11/04; C02F 11/12; C02F 2303/06; C02F 11/10; Y02E 50/343
USPC .................................................. 210/603, 609
See application file for complete search history.

(56) References Cited

U.S. PATENT DOCUMENTS

| | | | |
|---|---|---|---|
| 4,289,625 A | 9/1981 | Tarman et al. | |
| 4,522,151 A * | 6/1985 | Arbisi | A01K 63/042 119/228 |
| 4,880,473 A | 11/1989 | Scott et al. | |
| 5,017,196 A | 5/1991 | Dewitz | |
| 5,395,455 A | 3/1995 | Scott et al. | |

(Continued)

FOREIGN PATENT DOCUMENTS

| | | |
|---|---|---|
| BR | 9401102 A | 11/1994 |
| CA | 2628323 A1 | 6/2007 |

(Continued)

OTHER PUBLICATIONS

ASTM, Section D3172, Proximate Analysis of Coal and Coke, (2007), 2 pages.

(Continued)

*Primary Examiner* — Fred Prince

(57) ABSTRACT

Waste solids are treated by pyrolysis at a temperature over 700 degrees C. to produce char and a gas. The gas is treated in an anaerobic digester. In one system, gas and digestate are brought into contact in a diffusion cone. In another option, headspace gas above the digestate is re-circulated through the digestate, for example by way of an eductor downstream of the diffusion cone.

8 Claims, 1 Drawing Sheet

(56) References Cited

U.S. PATENT DOCUMENTS

| | | | |
|---|---|---|---|
| 5,417,492 | A | 5/1995 | Christian et al. |
| 5,424,417 | A | 6/1995 | Torget et al. |
| 5,605,551 | A | 2/1997 | Scott et al. |
| 5,865,898 | A | 2/1999 | Holtzapple et al. |
| 5,959,167 | A | 9/1999 | Shabtai et al. |
| 6,022,419 | A | 2/2000 | Torget et al. |
| 6,048,374 | A | 4/2000 | Green |
| 6,228,177 | B1 | 5/2001 | Torget |
| 7,229,483 | B2 | 6/2007 | Lewis |
| 7,494,637 | B2 | 2/2009 | Peters et al. |
| 7,578,927 | B2 | 8/2009 | Marker et al. |
| 7,608,439 | B2 | 10/2009 | Offerman et al. |
| 7,972,824 | B2 | 7/2011 | Simpson et al. |
| 8,383,871 | B1 | 2/2013 | Sellars et al. |
| 8,877,468 | B2 | 11/2014 | Lewis |
| 8,993,288 | B2 | 3/2015 | Lewis |
| 2003/0071372 | A1 | 4/2003 | Scherzinger et al. |
| 2004/0084366 | A1 | 5/2004 | Anderson et al. |
| 2006/0112639 | A1 | 6/2006 | Nick et al. |
| 2006/0289356 | A1 | 12/2006 | Burnett et al. |
| 2007/0117195 | A1 | 5/2007 | Warner et al. |
| 2007/0217995 | A1 | 9/2007 | Matsumura et al. |
| 2008/0035561 | A1 | 2/2008 | Gray |
| 2008/0236042 | A1 | 10/2008 | Summerlin |
| 2008/0280338 | A1 | 11/2008 | Hall et al. |
| 2009/0151253 | A1 | 6/2009 | Manzer et al. |
| 2009/0229595 | A1 | 9/2009 | Schwartz, Jr. |
| 2009/0239279 | A1 | 9/2009 | Hall et al. |
| 2010/0021979 | A1 | 1/2010 | Facey et al. |
| 2010/0133085 | A1 | 6/2010 | Hutchins et al. |
| 2010/0162627 | A1 | 7/2010 | Clomburg, Jr. et al. |
| 2010/0223839 | A1 | 9/2010 | Garcia-Perez et al. |
| 2010/0317070 | A1 | 12/2010 | Agaskar |
| 2011/0033908 | A1 | 2/2011 | Cheong et al. |
| 2011/0179700 | A1 | 7/2011 | Monroe et al. |
| 2011/0248218 | A1 | 10/2011 | Sutradhar et al. |
| 2012/0073199 | A1 | 3/2012 | Lewis |
| 2012/0322130 | A1 | 12/2012 | Garcia-Perez et al. |
| 2013/0134089 | A1 | 5/2013 | Cote |
| 2013/0203144 | A1* | 8/2013 | Josse ............... C02F 11/04 435/167 |
| 2013/0316428 | A1 | 11/2013 | Gonella |

FOREIGN PATENT DOCUMENTS

| | | | |
|---|---|---|---|
| CA | 2641270 | A1 | 12/2009 |
| DE | 10107712 | A1 | 9/2002 |
| EP | 0521685 | A2 | 1/1993 |
| EP | 1207040 | A2 | 5/2002 |
| EP | 1568478 | A1 | 8/2005 |
| GB | 1571886 | A | 7/1980 |
| GB | 2257137 | A | 1/1993 |
| GB | 2332196 | A | 6/1999 |
| JP | 2003089793 | A | 3/2003 |
| WO | 0179123 | A1 | 10/2001 |
| WO | 2004060587 | A1 | 7/2004 |
| WO | 2006056620 | A1 | 6/2006 |
| WO | 2010001137 | A2 | 1/2010 |
| WO | 2012166771 | A2 | 12/2012 |
| WO | 2013110186 | A1 | 8/2013 |
| WO | 2015050433 | A1 | 4/2015 |
| WO | 2015053617 | A1 | 4/2015 |

OTHER PUBLICATIONS

AWWTA, Standard Methods, Section 240G, (2000).
Bredwell et al., "Reactor Design Issues for Synthesis-Gas Fermentations, Biotechnology Process," Biotechnology Process, 1999, vol. 15 (5), pp. 834-844.
Cozzani et al., "A Fundamental Study on Conventional Pyrolysis of a Refuse-Derived Fuel," Industrial & Engineering Chemistry Research, Jun. 1995, 34, pp. 2006-2020.
Demirbas et al., "Biomass Resource Facilities and Biomass Conversion Processing for Fuels and Chemicals," Energy Conversion and Management, Jul. 2001, vol. 42 (11), pp. 1357-1378.
Demirbas et al., "The Influence of Temperature on the Yields of Compounds Existing in Bio-Oils Obtained from Biomass Samples via Pyrolysis," Fuel Processing Technology, Jun. 2007, vol. 88 (6), pp. 591-597.
European Patent Application No. 13740592, Supplementary European Search Report dated Jul. 27, 2015.
European Patent Application No. 16162806, Extended European Search Report dated Dec. 14, 2016.
Excerpts from Traite De Polarimetrie, Georges Bruhat, Paris, France, 1930.
Garcia-Perez, "Challenges and Opportunities of Biomass Pyrolysis to Produce Second Generation Bio- fuels and Chemicals," Auburn University, Jun. 13, 2012, 66 pages.
Guiot et al., "Potential of Wastewater-Treating Anaerobic Granules for Biomethanation of Synthesis Gas," Environmental Science and Technology, Feb. 2011, vol. 45 (5), pp. 2006-2012.
Gullu et al., "Biomass to Methanol via Pyrolysis Process," Energy Conversion and Management, Jul. 2001, vol. 42 (11), pp. 1349-1356.
International Patent Application No. PCT/CA2013/050037, International Preliminary Report on Patentability dated Aug. 7, 2014.
International Patent Application No. PCT/CA2013/050037, International Search Report dated Apr. 4, 2013.
International Patent Application No. PCT/CA2014/050662, International Preliminary Report on Patentability dated Jan. 21, 2016.
International Patent Application No. PCT/CA2014/050662, International Search Report and Written Opinion dated Sep. 25, 2014.
International Patent Application No. PCT/CA2016/050103, International Search Report and Written Opinion dated May 26, 2016.
Jenkins, "Oxidation-Based Water-Reuse Technology that Improves Mass Transfer," Chemical Engineering, Feb. 2013, p. 12.
Jones, et al., "Production of Gasoline and Diesel from biomass via Fast Pyrolysis" Hydrotreating and Hydrocracking: A Design Case, U.S. Department of Energy, PNNL-18284 Feb. 28, 2009, 76 pages.
Laemsak, "Wood Vinegar Presentation," Undated, 5 pages.
Laird et al., "Sustainable Alternative Fuel Feedstock Opportunities, Challenges and Roadmaps for Six U.S. Regions," Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010, pp. 257-281.
Lehmann et al., "Bio-Char Sequestration in Terrestrial Ecosystems—A Review ," Mitigation and Adaptation Strategies for Global Change , Mar. 2006, vol. 11 (2), pp. 403-427.
Lewis et al., "A Powerful by Product," WEFTEC, Jan. 2008, pp. 64-69.
Lian et al., "Separation, Hydrolysis and Fermentation of Pyrolytic Sugars to Produce Ethanol and Lipids," Bioresource Technology, Dec. 2010, vol. 101 (24), pp. 9688-9699.
Liaw et al., "Effect of Pyrolysis Temperature on the Yield and Properties of Bio-oils Obtained From the Auger Pyrolysis of Douglas Fir Wood," Journal of Analytical and Applied Pyrolysis, Jan. 2012, vol. 93, pp. 52-62.
Linden et al., "Gaseous Product Distribution in Hydrocarbon Pyrolysis," Industrial and Engineering Chemistry, 1955, vol. 47 (12), pp. 2470-2474.
Mahulkar et al., "Steam Bubble Cativation," AIChE Journal, Jul. 2008, vol. 54 (7), pp. 1711-1724.
Melin et al., "Evaluation of Lignocellulosic Biomass Upgrading Routes to Fuels and Chemicals," Cellulose Chemistry and Technology, 2010, vol. 44 (4-6), pp. 117-137.
Parry, Biosolids Technology Advances, Jan. 2012, 20 Pages.
Parry, et al. "Prolysis of Dried Biosolids for Increased Biogas Production" Proceedings of the Water Environment Federation, Residuals and Biosolids, Mar. 2012, pp. 1128-1139.
U.S. Appl. No. 14/631,144, Notice of Allowance dated Apr. 15, 2016.
U.S. Appl. No. 14/373,714, Office Action dated Jul. 24, 2015.
Shanley Pump and Equipment, Inc., EDUR Pumps, [online], printed May 30, 2014. Retrieved from the Internet.

(56) References Cited

OTHER PUBLICATIONS

Smith et al., "Integrating Pyrolysis and Anaerobic Digestion," The Northwest Bio-energy Symposium, Seattle, Washington, Nov. 13, 2012, 44 pages, http://www.pacificbiomass.org/documents/Smith.pdf.
Sustarsic, "Wastewater Treatment: Understanding the Activated Sludge Process" CEP Nov. 2009, pp. 26-29.
U.S. Appl. No. 13/136,180, Notice of Allowance dated Jul. 8, 2014.
U.S. Appl. No. 13/136,180, Notice of Allowance dated Mar. 4, 2014.
U.S. Appl. No. 13/136,180, Office Action dated Mar. 20, 2013.
U.S. Appl. No. 13/136,180, Office Action dated Nov. 2, 2012.
U.S. Appl. No. 13/826,507, Advisory Action dated May 22, 2015.
U.S. Appl. No. 13/826,507, Notice of Allowance dated Sep. 29, 2016.
U.S. Appl. No. 13/826,507, Office Action dated Feb. 26, 2016.
U.S. Appl. No. 13/826,507, Office Action dated Jul. 7, 2014.
U.S. Appl. No. 13/826,507, Office Action dated Mar. 18, 2015.
U.S. Appl. No. 13/826,507, Restriction Requirement dated Apr. 11, 2014.
U.S. Appl. No. 14/031,758, Notice of Allowance dated Nov. 28, 2014.
U.S. Appl. No. 14/031,758, Office Action dated Apr. 28, 2014.
U.S. Appl. No. 14/373,714, Notice of Allowance dated Nov. 10, 2015.
U.S. Appl. No. 14/631,144, Office Action dated Nov. 12, 2015.
U.S. Appl. No. 14/903,904, Office Action dated Jan. 17, 2017.
U.S. Appl. No. 15/085,381, Office Action dated Apr. 19, 2017.
Zhang et al., "Influence of Manure Types and Pyrolysis Conditions on the Oxidation Behavior of Manure Char," Bioresource Technology, Sep. 2009, vol. 100 (18), pp. 4278-4283.
Water and Sewage Treatment Energy Management Joint Conference, Delaware Valley Regional Planning Commission, Apr. 25, 2012, 55 Pages.
Written Opinion for Application No. PCT/CA2013/050037, dated Apr. 4, 2013, 7 pages.
Yang et al., "Pretreatment: The Key to Unlocking Low-Cost Cellulosic Ethanol," Biofuels, Bioproducts and Biorefinering, Jan. 2008, vol. 2 (1), pp. 26-40.
Zanzi et al., "Rapid Pyrolysis of Agricultural Residues at High Temperature," Biomass and Bioenergy, Nov. 2002, vol. 23 (5), 4 pages.

\* cited by examiner

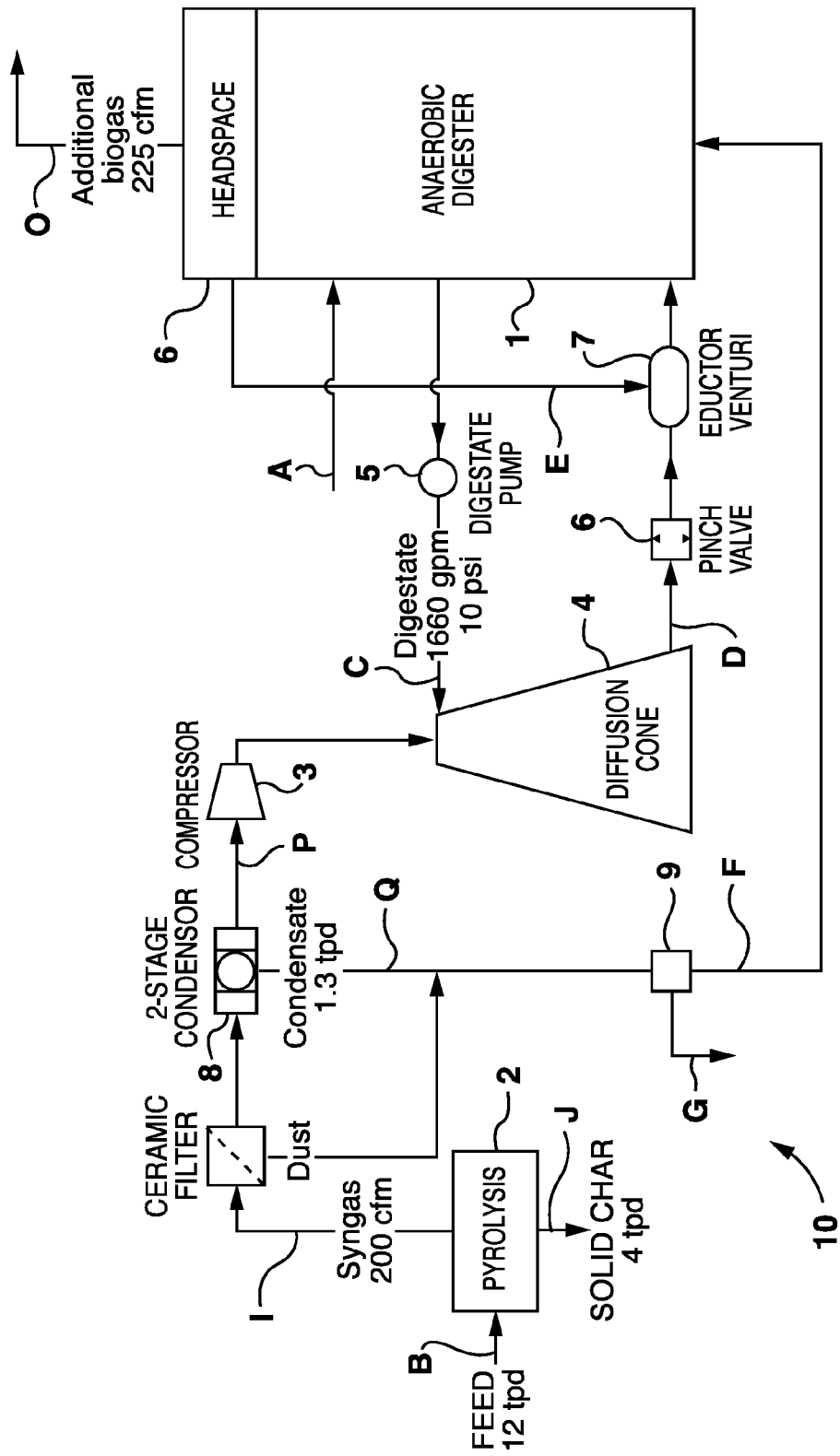

SOLID WASTE TREATMENT WITH CONVERSION TO GAS AND ANAEROBIC DIGESTION

CROSS-REFERENCE TO RELATED APPLICATIONS

This application claims the benefit of U.S. Application Ser. No. 62/112,948, filed Feb. 6, 2015. U.S. Application Ser. No 62/112,948 is incorporated by reference.

FIELD

This specification relates to solid treatment involving conversion to gas and biomethanation.

BACKGROUND

The following discussion is not an admission that anything discussed below is common general knowledge or citable as prior art.

Municipal sewage is often treated in activated sludge wastewater treatment plants. These plants produce treated effluent but also produce waste sludge, which may be primary sludge or waste activated sludge or both. The waste sludge is often treated as a form of solid waste, often referred to as biosolids. To reduce its volume, the sludge may be dewatered, and optionally dried. However, the waste sludge still creates a significant haulage and disposal problem.

As an example, California generated 797,000 dry tons of biosolids from wastewater treatment facilities in 2013. Roughly two thirds of this waste was applied to land and one third was landfilled. California has a goal of diverting 75% of the waste currently being landfilled. This goal applies to biosolids and to roughly 30 million tons of municipal solid waste (MSW) that is landfilled in California annually. For the biosolids, one possible response is to apply more of the biosolids to land. However, while federal regulations control the quality of biosolids that can be land applied to some extent, there is still concern that biosolids can contain Constituents of Emerging Concern (CEC) that are not regulated. CECs include, for example, pharmaceuticals, unregulated industrial and agricultural products, newly registered pesticides, detergents, fragrances, and hormones. There is also concern that biosolids can run off the soil to pollute natural water resources, and many residents simply object to the smell. As a result, several counties have passed bans prohibiting or restricting the application of biosolids to land.

Some wastewater treatment plants have an anaerobic digester that further treats the waste sludge. Anaerobic digestion produces biogas as a result of the biological fermentation of volatile solids (VS) supplied with the feedstock. Typical digesters treating sludge produced in a wastewater treatment plant achieve about 50% VS destruction in 20 day hydraulic retention time (HRT) mesophilic digesters. The digester sludge, or digestate, produced by an anaerobic digester is a combination of inert solids that were fed with the feedstock, recalcitrant volatile solids that could not be degraded biologically, and bacterial biomass that grew as a result of feeding on the degradable portion of the volatile solids in the feedstock. Waste digestate is typically dewatered and optionally dried. This produces another form of biosolids, but the mass of solids that needs to be disposed of is reduced relative to the original waste sludge. Anaerobic digesters are used at only some wastewater treatment plants since, for example, the required land is not always available and the cost of the digester is not always justified, particularly for small wastewater treatment plants.

Organic material can be treated with pyrolysis to generate gas, liquid a solid products. The solid product can be referred to as char, biochar or charcoal. The liquid products include a large number of chemical species including various alcohols, acids, and long chain hydrocarbons. Wood is a preferred feedstock because of its high heat value, low ash content, and availability. Recently developed systems focus on maximizing conversion to a long chain hydrocarbon rich liquid known as "bio-oil" through processes referred to as fast pyrolysis or flash pyrolysis, which occur at moderate temperatures (about 450-550° C.) and short residence times. The short residence times inhibit further decomposition of the bio-oil to other products. However, the bio-oil is diluted with the water from the feedstock and requires treatment to remove impurities in order to recover a liquid fuel. The value of the oil as a fuel does not always justify the cost in treatment and purification.

U.S. Pat. No. 8,877,468 describes a process in which materials containing lignocellulose are treated by pyrolysis under conditions (low temperature and long residence time) that favour the production of a liquid containing organic acids and alcohols. This liquid is suitable for conversion to biogas (primarily methane) in an anaerobic digester. In contrast, bio-oil produced by fast pyrolysis contains significant concentrations of compounds that are toxic to bacteria in an anaerobic digester. U.S. Patent Publication 2012/0322130 describes a system in which liquid pyrolysis products are separated into bio-oil and light oxygenated organic compounds. With the bio-oil removed, the light oxygenated organic compounds can be converted to biogas in an anaerobic digester.

The Applicant is involved in a demonstration project with the Encina Wastewater Authority to treat biosolids by pyrolysis according to a process as described in U.S. Pat. No. 8,877,468. In this demonstration project, dried waste sludge pellets are treated by pyrolysis at about 300-320 degrees C. to produce mostly char and a liquid. The char is applied to land. The liquid is co-digested with liquid waste sludge in an anaerobic digester and thereby converted into biogas. This demonstration project provides two primary benefits. Firstly, char is preferable to biosolids when applied to land. Char is odorless and free of living pathogens. Char sequesters carbon in the soil and improves the physical structure of soil rather than rotting on the land. Secondly, to the extent that some of the biosolids are converted into biogas, a waste product is converted into a source of energy.

INTRODUCTION

The following introduction is intended to introduce the reader to the detailed description and claims to follow, but is not intended to limit or define the claims.

In a system and process described in this specification, solid waste is converted into, among other things, a gas including hydrogen, carbon monoxide or both. The gas is dissolved into a liquid flowing into an anaerobic digester. The liquid may be, for example, water or a liquid feed stream being added to the digester or sludge drawn from the digester in a sidestream loop. In one example, the gas is dissolved into the liquid in a pressurized vessel such as a dissolution cone. The vessel may be pressurized in part by pumping liquid through the vessel against a downstream eductor that also draws gas form the digester into the liquid.

Dissolving the gas into the liquid flowing into the digester makes the gas available for conversion into biogas in the digester.

This specification also describes a system and process for treating solid waste using high temperature pyrolysis. The sold waste is treated by pyrolysis at a temperature over 700 degrees C., preferably over 750 degrees C., to produce solid, liquid and gas products. The liquid and gas products are removed from the system. The gas may be treated in an anaerobic digester, preferably as described above. Optionally, the solid waste may include one or more non-biogenic materials such as plastic.

This system also describes a system and process for controlling the addition of carbon monoxide to an anaerobic digester. The carbon monoxide concentration in the digester is monitored and compared to one or more selected values related to carbon monoxide inhibition or toxicity. Results of the comparison are considered in determining the rate at which carbon monoxide is added to the digester.

BRIEF DESCRIPTION OF THE FIGURES

FIG. 1 is a schematic process flow diagram of a solid waste treatment system.

DETAILED DESCRIPTION

Generally speaking, the systems and processes described herein convert one or more types of solid waste into methane. The solid waste is first converted, at least in part, into a gas containing carbon monoxide and hydrogen. The gas is fed into an anaerobic digester, preferably for co-digestion with other waste. In the digester, microorganisms convert the carbon monoxide and hydrogen contained in the gas, optionally in combination with the co-digested waste, to methane. Other compounds in the gas, such as methane, ethane, ethylene, carbon dioxide and nitrogen, are not necessarily converted to methane, but may become part of a biogas produced in the digester.

A preferred method of converting solid waste to gas is high temperature pyrolysis. In this case, pyrolysis is distinguished from gasification, which may occur at similar temperatures. In pyrolysis, some oxygen may be entrained with feedstock as air or water but material amounts of oxygen are not otherwise added into the process. As a result, char is produced, typically making up at least 5 or 10% of the products on a mass basis. In contrast, oxygen is added in gasification, either as compressed air or oxygen and water, to convert substantially all available carbon into gas or provide direct heating by combustion or both.

Pyrolysis is often described as occurring at temperatures of about 600 or 700 degrees C. or less. However, pyrolysis can also occur at higher temperatures. High temperature (HT) pyrolysis occurs above 700 degrees C., up to about 1000 degrees C. The dwell time may be 15 to 30 minutes. HT pyrolysis may be done in rotary kiln or screw type reactors, preferably heated with electricity, although indirect heating with flue gas is also possible. At high temperatures, air entrained with feedstock can cause combustion in the pyrolysis reactor. However, the risk of combustion can be reduced if necessary by removing entrained air from the feedstock, for example by compacting the feedstock, vacuum extraction or nitrogen blanketing.

HT pyrolysis produces solid, liquid and gas products with the gas product typically making up the largest percentage of the products by mass. Some researchers and companies have proposed to use the permanent gas produced in HT pyrolysis gas, after particle filtration and condensation, to fuel gas engines directly. However, the quality of the gas produced from when processing some feedstocks such as refuse derived fuel (RDF) is highly variable. The cost and complexity of the gas treatment system, and the need for specialized engines or burners, have so far prevented HT pyrolysis from being commercialized broadly but at least one commercial reactor is available. The design of another HT pyrolysis reactor is described by R. Zanzi et al. in "Rapid Pyrolysis of Agricultural Residues at High Temperatures."

More frequently, thermal processing practitioners have used gasification as a means to produce syngas for direct combustion or for further refining to produce liquid fuel. Gasification is preferred because converting the char increases the amount of gas produced per unit of feedstock. Although gasification can be used to produce a gas containing hydrogen and carbon monoxide, which can in turn be used to create methane in an anaerobic digester, pyrolysis is preferred in the systems and processes described in this application for two reasons.

Firstly, the ratio of carbon monoxide to hydrogen is generally higher after gasification than after HT pyrolysis. The relative increase in carbon monoxide in gasification results from the conversion of char. Carbon monoxide can be inhibitory in anaerobic digesters, particularly in the absence of hydrogen. Accordingly, more of the HT pyrolysis gas can be processed without creating carbon monoxide toxicity or inhibition problems. In addition, the presence of hydrogen promotes a biomethanation path that produces only methane whereas, when hydrogen is lacking, carbon monoxide is converted in part to methane and in part to carbon dioxide. The creation of char in HT pyrolysis is not considered to be a disadvantage since char has value and the char produced at high temperatures is particularly porous, which makes it useful as a soil-enhancing agent.

Secondly, in some gasification reactors air is used to supply oxygen to the gasification reactor. Nitrogen is introduced with the air in amounts that are much greater than even HT pyrolysis reactors with nitrogen blanketing of the feedstock. The intended gasses, hydrogen and carbon monoxide, are thereby diluted with nitrogen. In the systems and processes described herein, the intended gasses are dissolved into a liquid. Since this requires some energy, it is preferable to avoid diluting the intended gasses with large amounts of nitrogen.

The feedstock for HT pyrolysis can include, for example, cellulosic material such as wood chips, green waste and agricultural residues, waste sewage sludge biosolids, anaerobic digester sludge (digestate) biosolids. These types of feedstock are preferably dried to about 20% moisture content or less, for example about 15% moisture content, before feeding the pyrolyzer.

Another suitable feedstock for HT pyrolysis is refuse derived fuel (RDF), which is a combination of plastics, paper, and fibers, either in fluff or pelletized from. RDF is a product of processing municipal solid waste (MSW), either residential or commercial, typically after extracting recyclable materials, putrescible organics that can go directly to anaerobic digestion, and inerts. RDF fluff, typically light material shredded to 1" in size, has a low bulk density from 200 to 240 $kg/m^3$. This material can be compressed with screw-type feeders as it is fed to the pyrolyzer, such that the material density increases and equipment throughput are increased. Alternatively, the material can be pelletized, for example in a pellet mill.

The breakdown between char, permanent gas and condensate (liquid) products of HT pyrolysis vary depending on the feedstock material including its ash content, moisture content and calorific value. For instance, for wood chips with 15% moisture content and 14.5 MJ/kg calorific value, on a mass basis, about 70% becomes permanent gas, 12% char and fine particles, and 18% condensate after pyrolysis at 800 degrees C. The condensate is a combination of moisture in the feedstock and a small amount of oil and tars. An exemplary permanent gas composition for wood chip HT pyrolysis is: hydrogen $H_2$ (20%), carbon monoxide CO (30%), methane $CH_4$ (18%), ethane $C_2H_2$ (2%), ethylene $C_2H_4$ (2%) and carbon dioxide $CO_2$ (20%). Processing 1 metric ton/hr of wood chips with 15% moisture content produces approximately 900 $Nm^3$/hr of permanent gas and 100 kg/hr of char.

When digested sewage sludge biosolids is thermally dried to 90% TS content and a calorific value of 12 MJ/kg and subjected to pyrolysis at 800 degrees C., the product breakdown by mass is 42% permanent gas, 11% condensate and oil, and 37% char. The permanent gas has similar composition as the gas produced form wood pyrolysis.

For RDF with calorific value of 16 MJ/kg and about 15% moisture, the product breakdown after 800 degrees C. pyrolysis may be 74% permanent gas, 17% char, 9% condensate. The gas composition may be hydrogen $H_2$ (28%), carbon monoxide CO (20%), methane $CH_4$ (32%), ethane $C_2H_2$ (0.1%), ethylene $C_2H_4$ (0.1%) and carbon dioxide $CO_2$ (20%).

In the examples above, If nitrogen gas is used to create inert conditions, for example by displacing air from the feeding mechanism, purging the unit, or blanketing conveyors, it may appear in the permanent gas at about 8%. A smaller amount of volatilized nitrogen can also come from the feedstock.

The examples above also illustrate that HT pyrolysis produces significantly more gas and less liquid relative to pyrolysis at lower temperatures. In contrast, the method described in U.S. Pat. No. 8,877,468 provides a digestible liquid by way of pyrolysis at low temperatures. This is effective for biogenic materials, and a digestible liquid advantageously requires less energy to mix into a digester than a similar mass of a gas. However, the method is limited to biogenic materials such as the organics left in biosolids after anaerobic digestion or cellulosic or ligno-cellulosic material contained in wood, green waste, agricultural waste, paper and cardboard. When treating biogenic materials, the digestible liquid product advantageously requires less energy to mix into an anaerobic digester than a similar mass of gas. However, the process is somewhat limited to biogenic materials since non-biogenic materials such as plastics exhibit almost no effects of pyrolysis until they are exposed to higher temperatures, for example 400 or 500 degrees C.

It is desirable to be able to tolerate at least some non-biogenic material in the feedstock since a significant portion of solid waste contains at least some non-biogenic material. In particular, RDF may be mostly biogenic but still include non-biogenic wastes such as plastic bottles and packaging materials or synthetic fabrics. Although many non-biogenic materials are substantially converted to gas after pyrolysis at about 550 degrees C., pyrolysis with a mixture of biogenic and non-biogenic material in the feedstock at this temperature still creates liquid products with compounds that are toxic or inhibit growth of bacteria in an anaerobic digester in sufficient amounts. To increase the amount of solid waste that can be processed, liquid product containing these compounds is preferably removed from the process.

While pyrolysis liquids may contain some valuable chemicals, the systems and processes described in this specification are most likely to be used in a distributed manner associated with existing anaerobic digesters in agricultural or food processing facilities or, in particular, municipal waste water treatment plants. In this distributed context, the economies of scale required to process bio-oil on site are not likely to exist. For a system or process that will accept a mix of biogenic and non-biogenic feedstock, it is preferable to use HT pyrolysis to reduce the amount of bio-oil that will have to be transported somewhere else for processing.

With biogenic materials included in the feedstock, the ratio of gas to liquid pyrolysis products increases sharply at a temperature that is somewhere above 650 degrees C. and possibly as high as 800 degrees C. Pyrolysis above 650 degrees C. also minimizes the formation of polycyclic aromatic hydrocarbons (PAH) are formed primarily by pyrolysis in at temperatures ranging from 400 to 650 degrees C. while pyrolysis at 800 degrees C. or above can destroy or at least reduce the molecular weight of remaining PAH produced. Dioxin is also destroyed at 800 degrees C. In order to minimize the amount of liquid produced, and optionally its toxicity, it is preferred that HT pyrolysis occur at over 650 or 700 degrees C., preferably at 800 degrees C. or more.

The conversion of hydrogen and carbon monoxide to methane can proceed quickly but is limited by the mass transfer of gas to liquid since both gases have low dissolution coefficients. It is therefore desirable to dissolve at least some of the gas into the liquid and to minimize the size of entrained gas bubbles to increase surface area for transfer to the liquid. Smaller bubble size also increases the bubble hold up time in a digester tank and increases the ability for the gas to be dissolved in the liquid digester sludge where active bacteria can transform the CO and $H_2$ to methane.

CO and $H_2$ are both poorly soluble in solution. As a result, a large fraction of the gas does not dissolve in solution and instead exits the digester through the headspace with the biogas. Factors that increase mass transfer CO and $H_2$ include dissolving under pressure, using reactor configurations that maximize gas retention time, using gas recirculation loops to pass undissolved syngas from the reactor headspace back through the reactor liquid, using specially designed impellers and diffusers, and operating at lower temperature where gas solubility is higher (mesophilic at 38° C. vs. thermophilic at 55° C.) and lowering the viscosity of the liquid, which increases gas diffusivity, either with temperature, feedstock and feedstock blends, or pretreatment such as shearing or homogenization.

There are several methods that may be used to transfer gases to liquids. These include, for example, gas diffusers, microbbuble generation pumps, eductors, and saturation cones (also called dissolution cones). Introducing these gases into anaerobic digesters has the additional disadvantage of having to dissolve and disperse gas into viscous sludge and not clean water. This further hinders gas to liquid mass transfer. Saturation cones have been used to increase the dissolution of oxygen and ozone in water by using increased pressure and bubble retention time. In a system and process described herein, a gas such as HT pyrolysis permanent gas is added to a digester using a saturation cone. Digestate is drawn from the digester and pressurized by pumping it through a saturation cone in a recirculation side stream. Back pressure is created with a pinch valve or venturi or both downstream of the cone. Permanent gas is injected at the top of the cone and the high liquid velocity carries the gas downward into the lower portion of the cone with lower velocity. The effect of high pressure and the shape of the cone contribute to entraining and dissolving the gas in the downward circulating cone. The pressurized liquid exiting the cone has a high concentration of dissolved gases. As the recirculating digestate stream enters the digester near the bottom of the tank, the pressure drops and some microbubbles emerge from the liquid and rise slowly upward in the digester liquid column.

The diffusion cone is similar to equipment used to dissolve $O_2$ and ozone in water. In the diffusion cone, the gas and liquid are both pressurized. Digestate is pumped into the top of the cone and flows to the bottom of the cone. Syngas is pressurized and injected into the top of the cone and into the digestate. The pressure within the diffusion cone helps dissolves the syngas into the digestate. Pressure is supplied by the syngas compressor and by the digestate pump working against a pinch valve or another restrictor downstream of the exit of the cone.

While any other pressurized contact area could be used, the conical shape helps increase the residence time of syngas bubbles in the diffusion cone.

As the digestate travels downward, its velocity decreases because the cone is expanding. The reduced digestate velocity increases the time available for the gas to diffuse into the digestate. However, the rapid downward digestate flow at the top of the cone breaks up coalescing and rising gas bubbles and pushes them back down into the cone. Bubbles may move slowly down the cone or circulate within the cone until they dissolve or become so small that they are entrained even in the relatively slow moving liquid at the bottom of the cone. The digestate exits the bottom of the cone, optionally saturated with gas, and is injected back into the digester. At the entrance to the digester, the pressure drops and some of the syngas forms microbubbles. Bacteria in the digestate consume the gas dissolved in solution and the microbubbles.

Other methods of dissolving syngas gas into the digestate may also be used. For example, the syngas can be dissolved or entrained in the digestate with a diffuser, microbubble generator, eductor, pumped gas aspirator or a gas transfer membrane. A jet ejector pump or aspirator may be used to aspirate syngas. A pump recirculates sludge from the digester. This pump can be, for example, a chopper pump or an open impeller end suction centrifugal pump. The pump generates a primary flow. An ejector nozzle at the pump discharge reduces the pipe diameter and accelerates the sludge flow, lowering the pressure. This results in a secondary flow of syngas from the gas holder being drawn into the ejector. The turbulence in the ejector nozzle causes an active mixing zone where the liquid and gas are combined into a liquid jet containing fine syngas bubbles. The mixture exits in one or more locations around the lower third of the digester tank where jet nozzles are placed. This increases the mass transfer between gas and liquid and enables the syngas to dissolve in the digestate. Further, if the gas includes vapors, contact with the liquid condenses the vapors while heating the liquid.

An alternative method to create syngas microbubbles is to use a microbubble generator pump, such as made by Honda Pumps. These pumps are used for dissolved air flotation or ozone injection and create gas microbubbles of 50 micron diameter or less, which may be an order of magnitude smaller than bubbles produced by many gas eductors or aspirators. The microbubbles are dispersed in recirculating digestate or filtrate flow by connecting the pump gas inlet to the syngas storage holder. With smaller bubbles, the gas/water interface surface area is increased, gas holdup time in the water column also increases, and digester foaming is reduced.

Optionally, an eductor venturi is placed between the pinch valve and the digester. A gas inlet to the educator is connected to the headspace in the digester. The pressure drops across the eductor creates a vacuum on the top port. This vacuum draws gas from the headspace of the digester and injects it into the fluid stream. The eductor thereby uses some of the energy put into pumping the digestate to draw gas from the headspace with venturi effect and mix the headspace gas back into the digestate.

Alternatively, headspace gas may be recirculated in a separate sidestream loop or not at all. For example, biogas can be withdrawn from the headspace with a compressor and fed to a lance, air lift mixer, or other gas driven mixer in the digester to provide mixing as well as biogas recirculation. In other alternatives, any of the devices described for adding syngas to the digestate may be used to add biogas to digestate.

Recirculating headspace gas increases the residence time of the syngas. Some of the syngas that passed through the digester without being consumed by bacteria passes again through the system. The digestate, optionally saturated with syngas from the diffusion cone and pulling the biogas/syngas mix from the headspace, is injected into the digester. The pressure drop across the educator and additional pressure drop into the reactor allows some of the gas to form microbubbles and some remains dissolved. Bacteria consume the syngas dissolved in solution and the microbubbles and convert it into biogas methane. Syngas that is not consumed exits into the headspace and may get recirculated through the eductor although some will be removed with the biogas through the top of the reactor. However, in some cases enough syngas may be consumed in a single pass through the digester and headspace gas recirculation is not required.

In some cases, it may also be possible to use an educator for headspace gas recirculation and also to provide enough resistance to pressurize the diffusion cone without a pinch valve. It is preferred to have a pinch valve because it is controllable whereas the eductor is likely to have a fixed pressure drop at a given flow rate. However, if both a pinch valve and eductor are used, the eductor still contributes to providing resistance downstream of the diffusion cone and so the pinch valve does not need to provide as much resistance.

High-temperature pyrolysis of wastewater sludge coupled with pyrolysis gas (alternatively called syngas or producer gas) conversion to biogas through biomethanation achieves high temperature thermal treatment but avoids the costs involved in trying to burn pyrolysis gas. The mass of the feed can be reduced by 60-90%. High temperature pyrolysis also "cracks" volatile compounds to simple short-chain molecules. This reduces the risk of biological inhibition from toxic compounds that may be present in bio-oils generated from contaminated feedstocks.

In the digester, complex consortia of organisms present in anaerobic digesters convert organic compounds to $CH_4$ through hydrolysis, acidogenesis, acetogenesis, and methanogenesis. Large organic molecules are introduced to a digester and break down to smaller soluble organic molecules including sugars, amino acids, and fatty acids through hydrolysis. These soluble molecules are then converted to volatile fatty acids (VFAs) through acidogenesis. VFAs convert to acetic acid ($CH_3COOH$), $H_2$, and $CO_2$ through acetogenesis and subsequently to $CH_4$ and $CO_2$ through methanogenesis. CO and $H_2$ are feedstocks for the organisms that carry out acetogenesis (acetogens) and organisms that carry out methanogenesis (methanogens).

Acetogens and methanogens can convert the CO and $H_2$ present in syngas into $CH_4$. One pathway is where acetogens convert CO to acetate with $H_2O$ or $H_2$ as the co-reactant and methanogens subsequently convert the acetate to $CH_4$. An alternative pathway is where methanogens convert CO directly to $CH_4$ with $H_2O$ or $H_2$ as the co-reactant. For all pathways, methanogens ultimately generate the $CH_4$. The most thermodynamically favorable pathway is the direct reduction of CO with $H_2$: $CO+3H_2 \rightarrow CH_4+H_2O$ (G=−150 kJ/mol-CO). This pathway is assumed to dominant as long as $H_2$ is present. This pathway directly converts CO and $H_2$ to $CH_4$, without $CO_2$, and for this reason biomethanation increases the quality of biogas by generating a methane enriched gas stream. When $H_2$ is not present, the next most thermodynamically favorable reaction is direct reduction of CO with $H_2O$: $4CO+2H_2O \rightarrow CH_4+3CO_2$ (G=−53 kJ/mol-CO).

Inhibition of methanogens can begin to occur above 0.1 mM and becomes severe above 0.25 mM of CO. This means that at elevated CO concentrations, methane production may stop but production of acetate can continue. Inhibition over the course of hours and CO concentrations up to 0.8 mM is reversible, indicating that temporal accumulation of CO is not catastrophic to an anaerobic digester performing biomethanation. To mitigate this risk, CO is monitored, and the delivery of syngas is controlled, to ensure that the concentration in the liquid phase does not exceed inhibitory levels. One control method includes measuring the concentration of CO in the headspace and calculating the concentration of CO dissolved in the liquid with Henry's constant. Another method includes gas phase monitoring of $CH_4$ where decreases in $CH_4$ production indicate inhibition, or alternatively, monitoring one or more reaction intermediates such as acetic acid in the liquid phase where abrupt changes indicate inhibition. Another control strategy includes liquid phase monitoring by continuous or batch liquid grab samples where the concentration of CO is measured in the headspace by a variety of techniques that can include gas chromatography. In the event that an inhibitory concentration of CO is detected, the concentration can be reduced by one or more methods such as temporarily reducing or stopping input of syngas or the CO component of the syngas, adding supplemental hydrogen, adding or increasing recuperative thickening, bioaugmentation of the digester population, adding feedstock or water to dilute the contents of the digester, decreasing or stopping the recycled of headspace gas, evacuating or sweeping the headspace, and selectively removing CO from the headspace.

Gases present in syngas can be inhibitory. These gasses include ethylene (C2H4), ethane (C2H6), acetylene (C2H2), and even the reactant CO at elevated concentration. The risk of inhibition can be mitigated by using high-temperature filters or optimizing the pyrolysis process to minimize the production of these compounds or both. CO has been reported to be inhibitory at partial pressures above 0.1 atm. Therefore the process preferably maintains the CO concentration in the liquid below this value.

The word digestate is sometimes used to refer to only the solids fraction of the sludge produced by an anaerobic digester but in this specification digestate typically refers to the whole digester sludge.

FIG. 1 shows a system 10 for treating solid waste. The system 10 includes an anaerobic digester 1, alternatively referred to as a digester for brevity. The digester 1 is fed with a liquid waste A and a solid waste B. Liquid waste A may be, for example, industrial wastewater, slurried or diluted agricultural or food processing waste, or a sludge, for example primary or waste activated sludge or both from a wastewater treatment plant such as a municipal sewage plant. Solid waste B may be, for example, one or more biosolids (including waste digestate from the digester 1 itself); municipal solid waste; municipal yard waste; an industrial waste; or, an agricultural waste.

The digester 1 produces product biogas O which may, for example, be used to produce energy or upgraded to produce biomethane. The digester 1 may have one or more mixed covered tanks. Suitable digesters are sold under the Triton and Helios trade marks by UTS Biogas or Anaergia.

Sludge or digestate that will be used as solid waste B is preferably substantially dry, for example dried sludge pellets. Alternatively, sludge or digestate is treated in a mechanical dewatering unit, for example a centrifuge, filter press or screw press. The mechanical dewatering unit separates the digestate or sludge into a liquid fraction and a de-watered cake. The liquid portion, in some cases called a filtrate or centrate, may be discharged or re-used, optionally after further treatment. Optionally, the digester may be located near a municipal sewage treatment plant and the liquid portion may be returned to the municipal sewage treatment plant for further treatment. In this case, the digester preferably treats primary and waste activated (secondary) sludge from the sewage treatment plant either as some or all of the digester liquid waste A and optionally as some or all of solid waste B.

De-watered cake is preferably sent to a sludge cake dryer to reduce the water content of the cake before pyrolysis. Hot air and moisture produced by the dryer may be sent to a heat recovery treatment unit to extract waste heat for reuse, for example to help heat the digester 1, the pyrolysis reactor 2 or the dryer. The hot air and moisture may also be treated, for example to reduce odors, before it is discharged.

The sludge cake dryer produces a partially dried cake. Some or all of the partially dried cake may be sent to a pyrolysis reactor 2. Optionally, the pyrolysis reactor 2 may also be fed with alternative types of biomass, or a combination, for pyrolysis.

The pyrolysis reactor heats solid waste B to a temperature over 700 degrees C., preferably over 750 or 800 degrees C., in the absence or a deficiency of oxygen, to produce biochar J and hot syngas I. Optionally, biochar J may be used as a soil enhancer typically after being collected and stored temporarily and then hauled off site. Hot syngas may be sent to a gas heat exchanger to recover heat for re-used in the system or elsewhere. For example, recovered heat may be used to help heat the digester 1, the pyrolysis reactor 2 or a sludge dryer. Preferably, the biosolids are heated indirectly. Preferably, the amount of air entrained with waste solids entering the reactor is actively reduced, for example by compressing the solids, by removing the air such as by vacuum, or by replacing the air with another gas such as nitrogen.

Syngas I is preferably sent to a syngas condenser 8. The syngas condenser 8 separates the syngas I into a gas fraction P and a liquid fraction Q. The syngas condenser 8 does not necessarily condense all condensable gasses in the syngas I. Under some conditions, the liquid fraction Q might be sent to the digester 1. However, the liquid fraction Q is preferably sent to an oil-water separator 9 to produce a water fraction F and an organic fraction G. The water fraction F may contain some organic compounds and may discharged or re-used or sent to the digester 1 if it is sufficiently non-toxic or inhibitory, optionally after further treatment. The organic fraction G may include some water but contains a higher concentration of organic compounds than the liquid fraction.

The organic fraction may be disposed of, or treated or upgraded to produce usable products, either on site or after being removed to another facility. Alternatively, the organic fraction is returned to the pyrolysis reactor 2. In this alternative, in the absence of a practical or economical way to make a higher value use of the organic fraction, the amount of gas fraction sent to the digester 1 can be increased, which is may be preferable to sending the organic fraction to the digester 1 in a toxic or inhibitory form, disposing it, or transporting it to another facility.

The gas fraction P is sent to a compressor 3 and then to a diffusion cone 4. The diffusion cone 4 is also fed with digestate C supplied by a pump 5 from the digester 1. Syngas enriched digestate D passes through a pinch valve 6 and an eductor venturi 7 before returning to the digester 1. The eductor venturi 7 is also connected to a headspace of the reactor 1 and draws biogas E into the syngas enriched digestate D.

In one application, a municipal wastewater treatment plant or process such as an activated sludge plant is coupled with an anaerobic digester. Primary and waste activated (secondary) sludge from the wastewater treatment plant is sent to the digester as a liquid, optionally thickened. The digester produces digestate, which is de-watered to produce a cake. The digester sludge cake is further thermally dried and then fed to a high temperature pyrolysis system to produce syngas and char. The syngas is introduced into one or more digesters, for example the digester that produced the digestate, for bioconversion of syngas CO and $H_2$ into methane. Optionally, primary and secondary sludge may be fed (after suitable dewatering and optional drying) first to the pyrolysis system rather than being fed to the digester directly. The methane produced by the two processes in the digester combine in the digester headspace and may be used for energy generation with engines, turbines or fuel cells, or upgraded to biomethane for injection into the natural gas grid. The biochar resulting from the pyrolysis process may be used as soil enhancer. Compared to a system in which a digester merely treated sludge from the wastewater treatment plant, there may be less waste produced or the net energy consumption may be reduced, or both, per unit of sewage treated. Additional waste streams can be treated by pyrolysis to provide additional gas for biomethanation. Optional waste streams include biosolids produced from other wastewater treatment plants and yard waste. Another optional waste stream is RDF or any other derivative of MSW that includes non-biogenic waste. In this case in particular, the waste is preferably treated with HT pyrolysis, for example at about 750 or 800° C. or more. Adding the additional gas to the digester further increases biogas production.

We claim:

1. A process comprising steps of,
   a) producing a gas containing hydrogen and carbon monoxide from pyrolysis of a feedstock at a temperature of over 750 degrees C.; and,
   b) adding the gas to an anaerobic digester,
   wherein the feedstock comprises plastic.

2. The process of claim 1 wherein the feedstock comprises a mixture of biogenic and non-biogenic material.

3. The process of claim 1 wherein the anaerobic digester is coupled with or part of a municipal wastewater treatment plant.

4. The process of claim 1 comprising producing a gas containing hydrogen and carbon monoxide from pyrolysis of a feedstock at a temperature of 800 degrees C. or more.

5. An apparatus for transferring syngas to digestate comprising a diffusion cone in a sidestream loop wherein the diffusion cone defines an outer surface of part of the sidestream loop with a downwardly increasing cross sectional area.

6. The apparatus of claim 5 having an eductor in the sidestream loop downstream of the diffusion cone and connected to a headspace of the digester.

7. A process for treating wastewater comprising,
   a) treating the wastewater to generate a sludge;
   b) feeding the sludge to an anaerobic digester to produce biogas and digestate;
   c) dewatering the digestate to produce a cake;
   d) thermally drying the cake to produce a dried cake;
   e) pyrolysing the dried cake at a temperature of over 700 degrees C. or more to produce char and syngas;
   f) feeding the syngas to the anaerobic digester;
   g) monitoring one or more indicators of carbon monoxide inhibition in the anaerobic digester.

8. The process of claim 7 comprising pyrolysing the dried cake at a temperature of over 800 degrees C. or more.

* * * * *